United States Patent
Reinhardt et al.

(10) Patent No.: US 8,911,389 B2
(45) Date of Patent: Dec. 16, 2014

(54) KNEE-JOINT BANDAGE MADE OF ELASTIC MATERIAL AND WITH APPLICATION AID

(75) Inventors: Holger Reinhardt, Kempen (DE); Uwe Berendt, Luenen (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 117 days.

(21) Appl. No.: 13/496,719

(22) PCT Filed: Sep. 21, 2010

(86) PCT No.: PCT/EP2010/005773
§ 371 (c)(1),
(2), (4) Date: Oct. 26, 2012

(87) PCT Pub. No.: WO2011/035885
PCT Pub. Date: Mar. 31, 2011

(65) Prior Publication Data
US 2013/0053743 A1    Feb. 28, 2013

(30) Foreign Application Priority Data

Sep. 25, 2009 (DE) ...................... 20 2009 012 967 U

(51) Int. Cl.
  *A61F 5/00* (2006.01)
  *A61F 13/00* (2006.01)
  *A61F 13/06* (2006.01)
  *A61F 5/01* (2006.01)

(52) U.S. Cl.
  CPC ....... *A61F 13/061* (2013.01); *A61F 2005/0179* (2013.01); *A61F 2005/0176* (2013.01); *A61F 5/0109* (2013.01)
  USPC .................. 602/62; 602/26; 602/60; 602/61; 602/63

(58) Field of Classification Search
  USPC ................ 602/5, 23, 26, 60–63, 36; 128/882; D24/190–192
  See application file for complete search history.

(56) References Cited

U.S. PATENT DOCUMENTS

| 4,116,236 A | * | 9/1978 | Albert ............................. 602/26 |
| 4,445,505 A | * | 5/1984 | Labour et al. ................... 602/26 |
| 5,730,710 A | * | 3/1998 | Eichhorn et al. ................ 602/26 |
| D444,563 S | * | 7/2001 | Rodgers ....................... D24/190 |

(Continued)

FOREIGN PATENT DOCUMENTS

| DE | 36 37 879 | 5/1988 |
| WO | WO 00/49982 | 8/2000 |

OTHER PUBLICATIONS

International Search Report in the corresponding patent application PCT/EP2010/005773 mailed Dec. 28, 2010.

(Continued)

*Primary Examiner* — Kim M Lewis
(74) *Attorney, Agent, or Firm* — Juan Carlos A. Marquez; Bacon & Thomas PLLC

(57) ABSTRACT

A knee joint bandage (1) is made of elastic material and has a pad assigned to the knee cap. The bandage is provided, on at least one side of the pad, with a flexible stabilizing rod (8,9) that extends along the length of the bandage. The stabilizing rod (8,9) is provided with a grip part and is embedded in a pocket arranged on the bandage (1) and which is firmly connected to the material of the bandage (1) at edge zones (10, 11) and at the end of the bandage arranged above the knee cap.

5 Claims, 2 Drawing Sheets

(56) References Cited

U.S. PATENT DOCUMENTS

| | | | |
|---|---|---|---|
| 8,579,843 B2 * | 11/2013 | Bauerfeind et al. | 602/26 |
| 2006/0041214 A1 * | 2/2006 | Reinhardt et al. | 602/60 |
| 2007/0106191 A1 | 5/2007 | Mueller et al. | |
| 2008/0139985 A1 * | 6/2008 | Gilmour | 602/26 |
| 2012/0220910 A1 * | 8/2012 | Gaylord et al. | 602/16 |

OTHER PUBLICATIONS

International Preliminary Report in the corresponding patent application PCT/EP2010/005773 mailed Apr. 12, 2012.

Office Action from China State Intellectual Property Office, in corresponding Chinese Patent Application No. 201080042661.0, dated Dec. 20, 2013, pp. 1-5.

* cited by examiner

KNEE-JOINT BANDAGE MADE OF ELASTIC MATERIAL AND WITH APPLICATION AID

The invention relates to a knee-joint bandage made of elastic material and having a pad assigned to the knee cap, which bandage is provided on at least one side of the pad, with a flexible stabilizing rod that extends along the length of the bandage.

Such a bandage is shown and described in DE 36 37 879 A1. This bandage is provided with spring strip rods which extend practically across the whole length of the bandage and particularly support the knee-joint during bending thereof.

Such knee-joint bandages more or less tightly span the knee-joint depending on the elasticity of the bandage material which results in that application of the bandage and slipping it up across the heel and the knee-joint, is made difficult and requires a substantial force effort in any case. For facilitating the application of such a knee-joint bandage, one has already proposed according to WO 00/49982 to provide one or several loops at the upper edge of the knee-joint bandage in order to grip into these loops with a finger and then to pull them up whereby the bandage stitched to the loops is pulled along and can be slipped across the knee. For this purpose, a very solid connection, between the loop and the material of the knee-joint bandage is required so that the loop cannot break away upon pulling up the bandage.

It is the object of the invention to facilitate the application of such a knee-joint bandage with the required security for the bandage material. According to the invention, this is done thereby that the eyelet comprises a thickening at its side remote from the stabilizing rod. Herein, the stabilizing rod is used with a double action, i.e., at the one hand, for stabilizing the knee-joint and, on the other hand, as application aid for which purpose the stabilizing rod is provided with a grip part which can easily be gripped and directly passes on to the bandage material a pulling force applied to it. Embedding the stabilizing rod into the pocket arranged at the bandage, lends a sufficiently strong connection of the stabilizing rod to the material of the bandage so that a pulling force excerpted to the grip part, may well be distributed over the bandage material, and, therefore, it is not subject to a particularly high additional stress upon application.

Herein, the stabilizing rod is, used in a double effect, i.e., on the one hand, for stabilizing the knee-joint and, on the other hand, as an application aid for which purpose the stabilizing rod is provided with a grip part which may easily be gripped and transfers a pulling force applied to it, directly to the bandage material.

Upon exerting a pulling force to the grip part, it is applied to the complete length of the bandage in this way.

The grip part is conveniently formed as an eyelet wherein the passage through its hole is located approximately at right angles to the bandage material. In case of such an arrangement of the grip part, it can be gripped directly with one finger which passes through the eyelet and transfers the pulling force conveniently to the bandage in this way. The gripping of the eyelet can further be facilitated thereby that it comprises a thickening on the side remote from the stabilizing rod.

An embodiment of the invention is shown in the figure.

Figure 1:
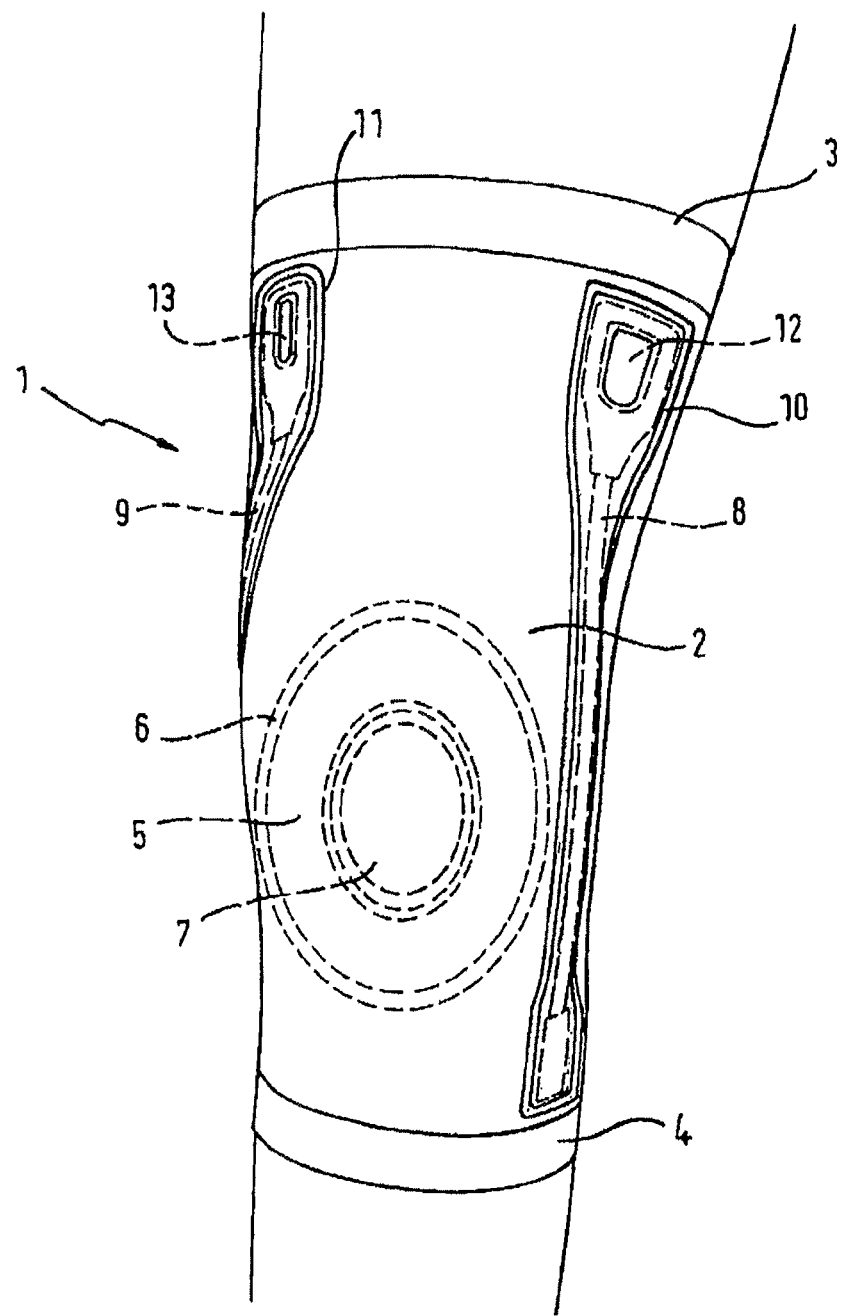
FIG. 1 shows a plan view onto the knee with applied knee-joint bandage.

The knee joint bandage 1 shown in FIG. 1, consists of the stocking 2 constructed out of elastic textile material, it is provided with the two edges 3 and 4 at its two ends which contribute to the slipping safety of the bandage 1. Furthermore, these edges 3 and 4 are produced out of a material which comprises a lower tension as compared to the stocking 2 in order to only slightly constrict the leg of the user at the respective positions. At the front side of the knee-joint, a profiled insert with a pad 5 is inserted into the stocking 2 which inserts consists, for example, out of foam material or silicon and has a substantial elasticity. The pad 5 is covered on the inner side of the stocking 2, by a cover which is connected, for example by gluing, at its edges 6 to the stocking 2. The pad 5 leaves free, at its central portion, an area into which the knee cap 7 approximately fits. The knee cap 7 is, thereby, embraced by the pad 5. In so far, a knee joint bandage arranged in a manner known per se is concerned.

Next to the pad 5, the bandage 1 is provided with two stabilizing rods 8 and 9 which extend essentially across the complete length of the bandage 1 and which provide for the bandage 1 applied to the leg, not being able to contract in its length direction. Each of the two stabilizing rods 8 and 9 is taken up in a pocket which is glued to the bandage 1 by means of the boarder zones 10 and 11, respectively, to the material of the bandage 1. Depending on the desired intensity of the stabilization, the bandage 1 may also be provided with one stabilizing rod only.

Figure 2:
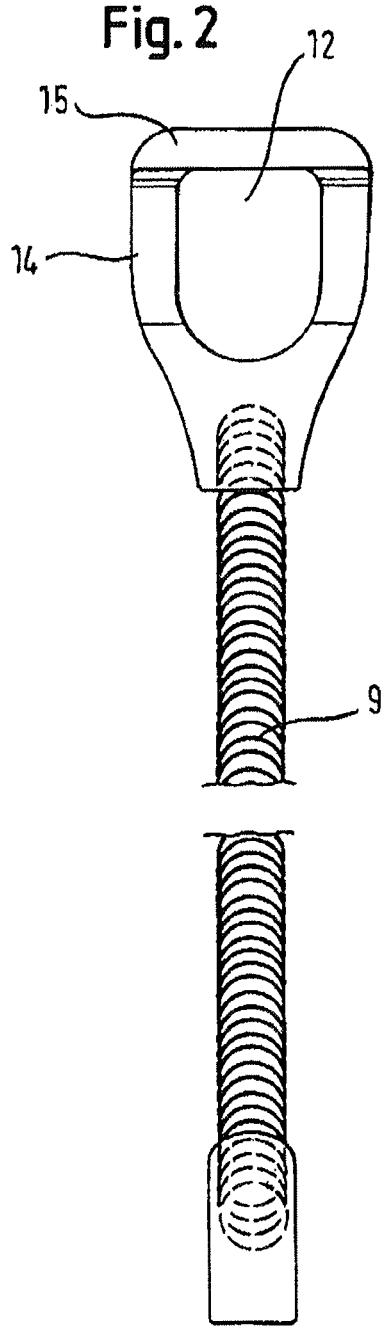
FIG. 2 shows the grip part alone in plain view onto the hole in the eyelet.
Figure 3:
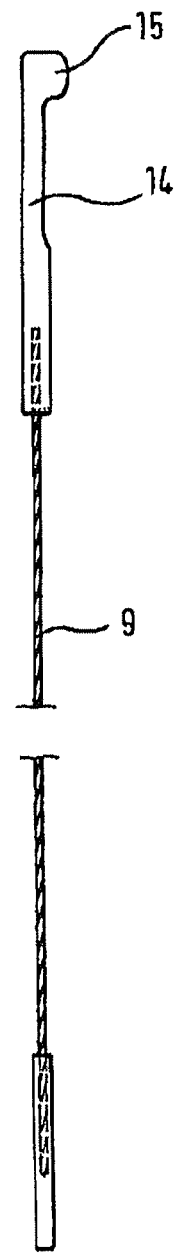
FIG. 3 shows the grip part according to FIG. 2 in side elevation.

In the FIGS. 2 and 3, it is referred in more detail to the specific arrangement of the stabilizing rods 8, 9 in the area of its grip part.

Each of the two stabilizing rods 8 and 9 comprises, at its upper end, a grip part 14 containing an eyelet 12 and 13, respectively, which grip part allows gripping the bandage 1 at its application and pulling up thereof along the leg with the finger and, thereby, facilitates the application of the bandage since the bandage 1 is a whole pulled along on application of a corresponding pulling force to the grip part 14 by them and the stabilizing rod 8, 9 whereby it is possible without further means to draw the bandage 1 smoothly across the food, the calf and the knee into its final position.

The stabilizing rods 8 and 9 contained in the pockets, are, thereby, tightly received by the respective pockets thereby that their edge zones 10 and 11 are formed each as a narrow circumferential strip which is directly connected to the material of the bandage, for example by welding or by gluing.

FIG. 2 shows a stabilizing rod 9 alone with the grip part 14 which comprises the eyelet 12. The grip part 14 consists out of an elastic plastic material, in its lower end, the actual stabilizing rod 9 is inserted and is tightly and in a pull prove manner gripped by the material of the grip part 14. The stabilizing rod 9 consists out of flat-pressed turns of a helical spring so that a substantial elasticity on bending is resulting while being secured against axial stretching, whereby the stabilizing rod 9 as applied to the bandage 1 can also bend.

FIG. 3 shows the grip part 14 with inserted stabilizing rod 9 in side elevation. It shows, at the upper end of the grip part 14, the thickening 15 which serves to give a good grip to a finger pushed into the eyelet 12 of the grip part 14 upon application of the bandage 1.

The invention claimed is:

1. Knee joint bandage constructed out of elastic material and having a pad configured for a knee cap, the bandage being provided, on at least one side of the pad, with a flexible stabilizing rod wherein the stabilizing rod is embedded in a pocket which is arranged on the bandage and which pocket is firmly connected to the material of the bandage at edge zones and at the end of the bandage located above the knee cap, the stabilizing rod having a grip part formed as an eyelet with a hole defined therein, wherein the stabilizing rod and the grip are embedded in the pocket.

2. Knee joint bandage according to claim 1, wherein the stabilizing rod is essentially continuously welded to the material of the bandage.

3. Knee-joint bandage according to claim 1, wherein the eyelet comprises a thickening at its side remote from the stabilizing rod.

4. Knee joint bandage according to claim 1, wherein the stabilizing rod is essentially continuously welded to the material of the bandage, and the eyelet comprises a thickening at its side remote from the stabilizing rod.

5. Knee-joint bandage according to claim 1, wherein the eyelet comprises a thickening at its side remote from the stabilizing rod.

* * * * *